US008444802B2

(12) United States Patent
Lee et al.

(10) Patent No.: US 8,444,802 B2
(45) Date of Patent: May 21, 2013

(54) CATHETER HAVING A READILY BONDABLE MULTILAYER SOFT TIP

(75) Inventors: Jeong S. Lee, Diamond Bar, CA (US); Kenneth L. Wantink, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 176 days.

(21) Appl. No.: 12/468,745

(22) Filed: May 19, 2009

(65) Prior Publication Data
US 2009/0223624 A1 Sep. 10, 2009

Related U.S. Application Data

(62) Division of application No. 11/738,260, filed on Apr. 20, 2007, now Pat. No. 7,549,975.

(51) Int. Cl.
*B32B 37/00* (2006.01)
*B29C 65/00* (2006.01)
*A61M 25/00* (2006.01)

(52) U.S. Cl.
USPC ............. 156/294; 156/308.2; 604/96.01

(58) Field of Classification Search
USPC ......... 156/293, 294, 308.2, 309.6; 604/96.01, 604/103; 606/194, 192
See application file for complete search history.

(56) References Cited

U.S. PATENT DOCUMENTS

| | | | |
|---|---|---|---|
| 4,921,483 A | 5/1990 | Wijay et al. | |
| 5,304,134 A * | 4/1994 | Kraus et al. | 604/96.01 |
| 6,368,301 B1 | 4/2002 | Hamilton et al. | |
| 6,530,938 B1 | 3/2003 | Lee et al. | |
| 6,692,461 B2 | 2/2004 | Wantink | |
| 6,837,869 B2 | 1/2005 | Hamilton et al. | |
| 6,918,920 B1 | 7/2005 | Wang et al. | |
| 7,115,137 B2 | 10/2006 | Duchamp | |
| 7,141,059 B2 | 11/2006 | Duchamp et al. | |
| 7,341,571 B1 | 3/2008 | Harris | |
| 2003/0032921 A1 | 2/2003 | Duchamp | |
| 2005/0131445 A1 | 6/2005 | Holman et al. | |

OTHER PUBLICATIONS

Merriam-Webster Dictionary Definiton of "fusion" 1997.*

* cited by examiner

*Primary Examiner* — John Goff
(74) *Attorney, Agent, or Firm* — Fulwider Patton LLP

(57) ABSTRACT

A balloon catheter having a soft distal tip member having a non-tacky inner (liner) layer material and a soft flexible outer layer material, with both materials being readily thermally bondable to the catheter balloon.

18 Claims, 2 Drawing Sheets

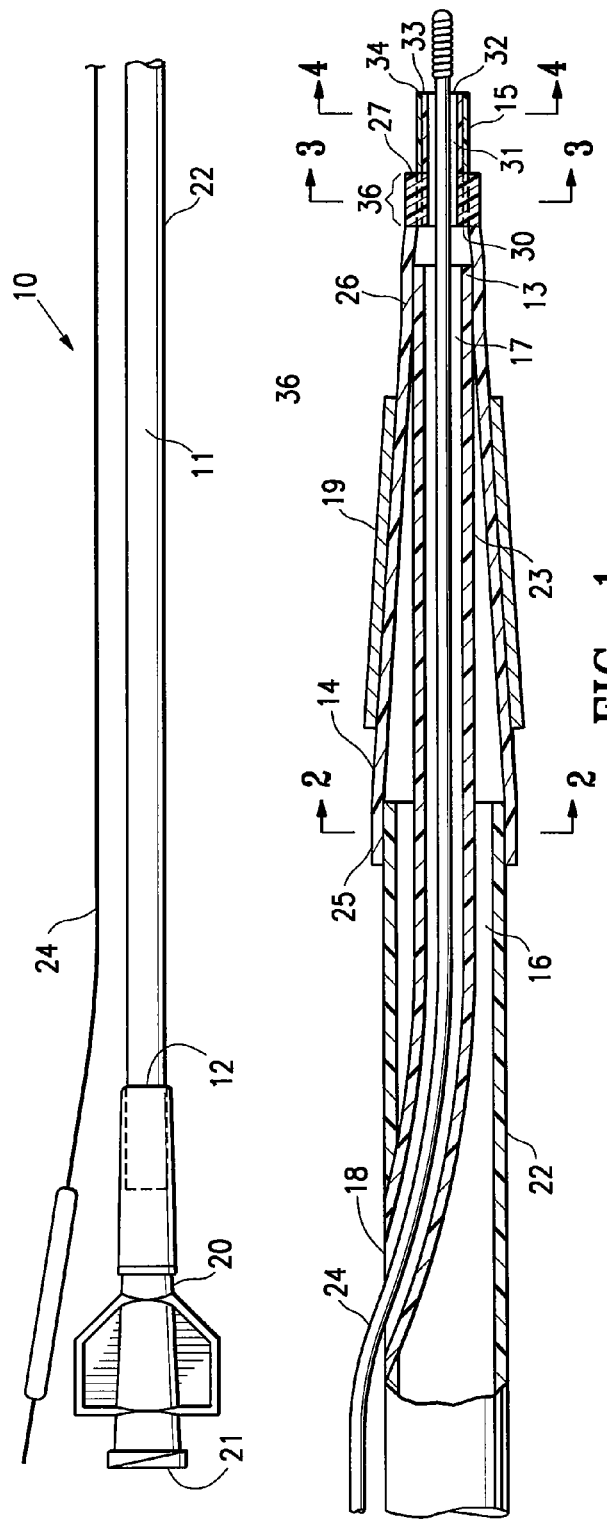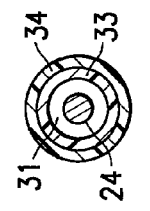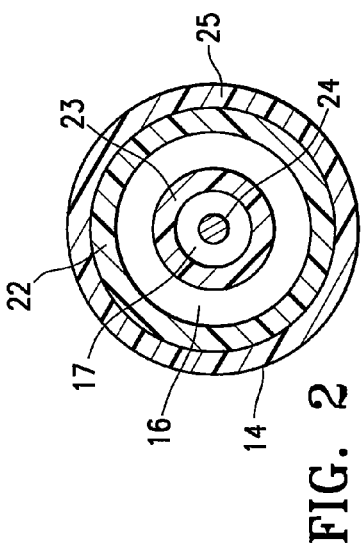

CATHETER HAVING A READILY BONDABLE MULTILAYER SOFT TIP

CROSS-REFERENCES TO RELATED APPLICATIONS

This application claims priority to U.S. Ser. No. 11/738,260, filed Apr. 20, 2007, now U.S. Pat. No. 7,549,975.

BACKGROUND OF THE INVENTION

This invention relates generally to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

An essential step in effectively performing a PTCA procedure is properly positioning the balloon catheter at a desired location within the coronary artery. To properly position the balloon at the stenosed region, the catheter shaft must be able to transmit force along the length of the catheter shaft to allow it to be pushed through the vasculature. However, the catheter shaft must also retain sufficient flexibility to allow it to track over a guidewire through the often tortuous vasculature. Additionally, the catheter must have good crossability (i.e., the ability of the catheter distal end to cross stenosed portions of the vascular anatomy).

Conventional intravascular catheters have commonly included a soft distal tip which prevents or minimizes injury to the vessel during advancement of the catheter therein. One difficulty has been the tendency of the soft tip materials to frictionally engage or stick to the guidewire (commonly referred to as "locking" of the guidewire), making it difficult to advance or retract the catheter. Additionally, in the design of soft tips, it is necessary to minimize the stiffness of the distal end of the catheter to aid in flexibly tracking the device during dilatation and stenting procedures, while nonetheless preventing structural failure/disengagement of the soft tip or kinking at the junction between the soft tip and catheter shaft.

Accordingly, it would be a significant advance to provide a catheter with a soft tip having improved performance. This invention satisfies these and other needs.

SUMMARY OF THE INVENTION

The invention is directed to a balloon catheter having a soft distal tip member having a non-tacky inner (liner) layer material and a soft flexible outer layer material, with both materials being readily thermally bondable to the catheter balloon. The tip is fusion bonded to the distal end of the balloon, in a configuration which preferably provides a securely bonded yet flexible and soft distal end with a non-tacky inner surface.

A catheter of the invention generally comprises an elongated catheter shaft, a balloon on a distal shaft section, and a distal tip member at a distal end of the catheter having an inner layer formed of a first polymeric material which has a first Shore durometer hardness and which defines at least a section of the lumen of the distal tip, and an outer layer formed of a second polymeric material which has a lower Shore durometer hardness than the first polymeric material and which is fusion bond compatible with the first polymeric material. More specifically, in one embodiment, the balloon catheter comprises an elongated catheter shaft having a proximal end, a distal end, a proximal shaft section, a distal shaft section, a guidewire receiving lumen extending along at least a distal portion of the catheter shaft, and an inflation lumen, and an inflatable balloon sealingly secured to the distal shaft section so that an interior of the balloon is in fluid communication with the shaft inflation lumen, and a distal tip member (having the inner layer formed of the first polymeric material and the outer layer formed of the second polymeric material) which has a proximal end longitudinally spaced distally apart from the distal end of the elongated catheter shaft with a gap therebetween, and a lumen which extends to a guidewire distal port in communication with the shaft guidewire lumen. The inflatable balloon has a distal skirt section fusion bonded to the proximal end of the tip, such that a proximal section of the tip is a fused blend of the balloon distal skirt section and the inner and outer layers of the tip, the fused blend having both the outer layer material and inner layer material of the tip fused with the material of the distal skirt section along at least the proximal section of the tip. In a presently preferred embodiment, the inflatable balloon is formed at least in part of the first polymeric material (i.e., the same polymeric material as the inner layer of the tip).

The first and second polymeric materials are preferably of the same polymer family, e.g., polyamides, and more preferably are of the same polymer type, e.g., a polyether block amide (PEBAX), although it should be understood that the first polymeric material has a different Shore durometer hardness than the second polymeric material such that the first and second polymeric materials are not the same polymeric material. In a presently preferred embodiment, the first and second polymeric materials are a polyamide such as a polyether block amide (PEBAX) copolymer or a nylon.

The first polymeric material is preferably a relatively high Shore durometer material providing a non-tacky inner surface along at least a section of the distal tip. For example, relatively high durometer polyamides are typically non-tacky whereas relatively low durometer polyamides are tacky (adhesive stickiness), at least at temperatures commonly encountered during assembly or use of the catheter. Such tacky materials have an increased risk of adhering to a processing mandrel during assembly of the catheter, potentially resulting in tearing/damage of the tip. Moreover, during use of the catheter in an interventional medical procedure, such tacky materials can cause "locking" of the guidewire, thus disadvantageously affecting deliverability of the catheter. However, unlike attempts to improve processability and deliverability of the catheter by having a distal end with an inner lubricious layer of a material such as high density polyethylene (HDPE) or polytetrafluoroethylene (PTFE) and an outer layer of a bondable material for heat fusion bonding to the balloon, both the inner and outer layers of the distal tip of the invention are individually heat fusion (i.e., thermally) bondable to the balloon (and do form a heat fusion bond to the balloon). As a result, tip integrity is improved in a catheter of the invention.

A method of making a catheter of the invention generally comprises positioning a proximal end of a distal tip member in contact with (e.g., within) a distal skirt section of the balloon and fusion bonding the distal tip to the distal skirt section, the distal tip member having coextruded inner and outer layers extending from the proximal end of the tip, and the inner layer is formed of a first polymeric material which has a first Shore durometer hardness, and the outer layer is formed of a second polymeric material which has a lower Shore durometer hardness than the first polymeric material and which is fusion bond compatible with the first polymeric material, and the balloon is formed at least in part of a polymeric material fusion bond compatible with the distal tip materials. The fusion bonding typically involves applying heat and an inward force on an outer surface of a distal portion of the balloon distal skirt section to fusion bond an inner surface of the distal skirt section to the proximal end of the distal tip member, such that a proximal section of the tip is a fused blend of the balloon distal skirt section and the inner and outer layers of the tip, the fused blend having both the outer layer and inner layer of the distal tip fused with the material of the distal skirt section along the proximal section of the tip. The method includes bonding the balloon distal skirt section of the elongated catheter shaft, typically by applying heat and a radially inward force on an outer surface of a proximal portion of the balloon distal skirt section, located proximal to the fusion bonded distal tip member, to bond the distal skirt section to the elongated shaft, such that the proximal end of the tip is longitudinally spaced distally apart from the elongated shaft by a gap there between.

A catheter of the invention has enhanced processability and deliverability due to the configuration of the multilayered distal tip. The soft distal tip provides a flexible, atraumatic distal end, with a non-tacky inner surface which prevents or inhibits "locking" of the guidewire during an interventional procedure, while nonetheless having a high pull strength for improved tip integrity. These and other advantages of the invention will become more apparent from the following detailed description and exemplary figures.

BRIEF DESCRIPTION OF THE DRAWINGS

FIG. 1 is an elevational partially in section view of a balloon catheter embodying features of the invention.

FIGS. 2, 3 and 4 are transverse cross sectional views of the balloon catheter of FIG. 1, taken along lines 2-2, 3-3 and 4-4, respectively.

DETAILED DESCRIPTION OF THE PREFERRED EMBODIMENTS

Figure 5B:
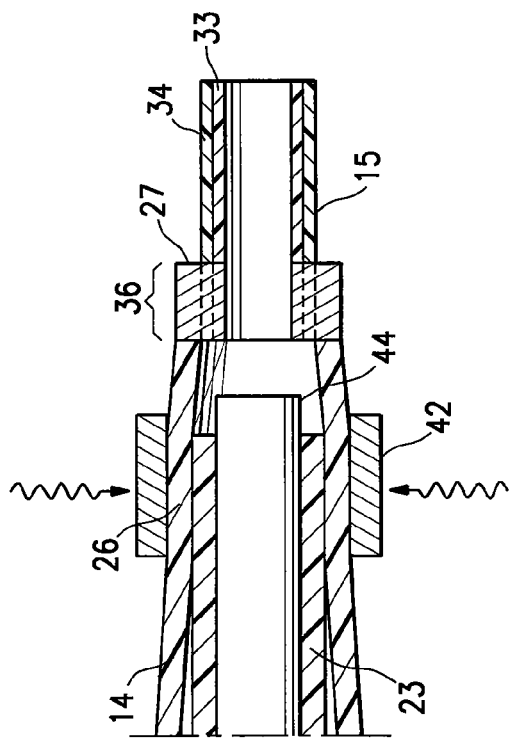
FIG. 5b illustrates the balloon catheter of FIG. 3a, after the fusion bonding of the distal tip member, during the fusion bonding of the distal skirt section to a shaft inner tubular member.

FIG. 1 illustrates a stent delivery balloon catheter 10 embodying features of the invention, generally comprising an elongated catheter shaft 11 having a proximal end 12 (within a strain relief/proximal adapter), a distal end 13, a proximal shaft section, a distal shaft section, an inflatable balloon 14 on the distal shaft section, and a distal tip 15 at a distal end of the catheter 10. The catheter shaft 11 has an inflation lumen 16 and a guidewire lumen 17. In the illustrated embodiment, the catheter 10 is a rapid exchange-type catheter with the guidewire lumen 17 extending along the distal shaft section to a guidewire proximal port 18 spaced distally from the proximal end 12 of the catheter shaft. At the proximal end 12, the shaft connects to strain relief tubing and a proximal adapter 20. The proximal adapter 20 has a port 21 in fluid communication with the inflation lumen 16 of the catheter shaft 11 and configured for connecting to a fluid source (not shown) for inflating/deflating the balloon 14. The balloon 14 is illustrated in a noninflated configuration in FIG. 1, with a radially expandable stent 19 mounted on the balloon 14. The distal end of catheter 10 may be advanced to a desired region of a patient's body lumen in a conventional manner with the balloon 14 in the low profile, noninflated configuration, and the balloon 14 inflated by directing inflation fluid into the balloon interior to radially expand the balloon and stent, and the balloon deflated for repositioning or removal from the body lumen, leaving the stent 19 implanted in the body lumen. The balloon 14 can be configured to perform a variety of medical procedures.

In the illustrated embodiment, the shaft 11 comprises an outer tubular member 22 having an inflation lumen 16 therein, and an inner tubular member 23 defining a guidewire lumen 17 therein configured to slidingly receive a guidewire 24. Specifically, the coaxial relationship between outer tubular member 22 and inner tubular member 23 defines annular inflation lumen 16, as best shown in FIG. 2 illustrating a transverse cross section of the catheter of FIG. 1, taken along line 2-2. The inflatable balloon 14 has a proximal skirt section 25 sealingly secured to the distal end of outer tubular member 22 and a distal skirt section 26 sealingly secured to the distal end of inner tubular member 23, so that the balloon interior is in fluid communication with inflation lumen 16.

The distal tip 15 has a proximal end 30 longitudinally spaced distally apart from the distal end 13 of the elongated catheter shaft inner tubular member 23 with a gap there between, and a lumen 31 which extends to a guidewire distal port 32 at the distal end of the tip 15. The distal tip lumen 31 and guidewire distal port 32 are communication with the shaft guidewire lumen 17 in the inner tubular member 23, so that the guidewire 24 is slidably disposed therein.

The distal tip 15 has an inner layer 33 formed of a first polymeric material which has a first Shore durometer hardness and which defines at least a section of the lumen 31 of the distal tip 15, and an outer layer 34 formed of a second polymeric material which has a lower Shore durometer hardness than the first polymeric material and which is fusion bond compatible with the first polymeric material. Preferably, the balloon 14 is formed at least in part of the first or the second polymeric material. More specifically, in one presently preferred embodiment, the balloon has at least a layer formed of the first polymeric material (i.e., of the same polymer material type and durometer hardness as the inner layer 33 of the distal tip 15). For example, in one embodiment, the balloon is a single layered balloon formed of the first polymeric material. However, catheter balloons can conventionally be formed of multiple materials, for example as a multilayered balloon. Thus, in an alternative embodiment, the balloon has an outer layer formed of the first polymeric material, and an inner layer formed of a different polymeric material.

In the embodiment of illustrated in FIG. 1, along a proximal section 36 of the distal tip 15, the distal tip 15 is fusion bonded to an inner surface of a distal end of the distal skirt section 26, such that the proximal end 30 of the distal tip 15 is surrounded by the distal skirt section 26. Both the inner layer 33 material and the outer layer 34 material of the tip 15 extend along the proximal section 36 of the tip 15, such that the proximal section 36 of the tip 15 is a fused blend of the balloon distal skirt section 26 and the inner and outer layers 33, 34 of the tip 15. Fusion bonding the inner surface of the distal skirt section 26 to the outer surface of the distal tip 15 causes the materials to soften or melt, and flow sufficiently such that the material of the inner layer 33 comes into contact with and fuses to the material of the distal skirt section 26, to form a fused blend of all three of the inner layer, outer layer, and distal skirt section materials. Thus, the fused blend has both the outer layer 34 material and inner layer 33 material of the tip 15 fused to the material of the distal skirt section 26 along the proximal section 36 of the tip 15. The terminology "inner layer 33 material" and "outer layer 34 material" should be understood to refer to the fused blend material at the proximal section 36 (which had the inner layer 33 and outer layer 34 extending therealong as discrete layers prior to fusion bonding to the balloon distal skirt section 26) which, after the fusion bonding, has the material of the inner layer 33 and the material of the outer layer 34 within the blended fusion bond without the defined structure of the original discrete layers.

The inner layer 33 material and the outer layer 34 material both extend to the proximal end 30 of the distal tip 15. Thus, the fused blend of all three materials (the inner layer 33 material, the outer layer 34 material, and the distal skirt section 26 material) extends along the entire length of the portion of the distal skirt section fusion bonded to the distal tip 15.

A distal section of the distal tip member 15 is located distal to the fused proximal section 36 of the tip 15 and balloon distal skirt section 26. Thus, a distal end 27 of the balloon distal skirt section 26 is proximally spaced from the distal end of the distal tip 15. FIG. 3 illustrates a transverse cross section along line 3-3 in FIG. 1 through the fused proximal section 36, and FIG. 4 illustrates a transverse cross section along line 4-4 in FIG. 1 through the distal section of the tip 15. In a presently preferred embodiment, the distal section of the tip 15 is longer than the fused proximal section 36 of the tip. For example, in one embodiment the fused proximal section 36 is about 10% to about 25% of the total length of the distal tip 15.

Figure 6:
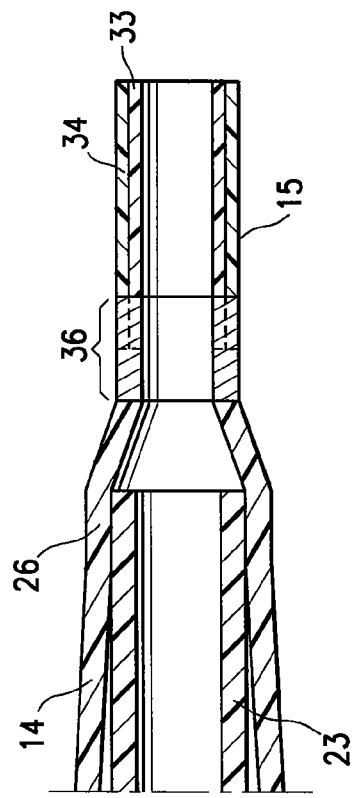
FIG. 6 illustrates the distal end of an alternative embodiment of a balloon catheter embodying features of the invention, in which the distal tip member is butt-joined to the distal skirt section of the catheter balloon.

In the embodiment illustrated in FIG. 1, the inner layer 33 and the outer layer 34 of the distal tip 15 form a lap joint to an inner surface of the distal skirt section 26, as opposed to a butt joint to the distal skirt section 26. As a result, at least a proximal portion of the balloon distal skirt section 26 surrounds the tip 15 and typically has a larger outer diameter than the distal section of the distal tip 15. Although the distal end 27 of the distal skirt section 26 is illustrated with a sharply squared surface in FIG. 1, it should be understood that it typically has a rounded and tapered outer surface after being bonded to the underlying distal tip 15. FIG. 6 illustrates an alternative embodiment, in which the proximal end of the distal tip 15 is butt joined to the distal end of the distal skirt section 26. The polymeric materials and fusion bonding are otherwise the same as the embodiment of FIG. 1, such that the embodiment of FIG. 6 similarly has the fused proximal section 36 formed of a fused blend of the balloon distal skirt section 26 and the inner and outer layers 33, 34 of the tip 15.

The Shore durometer hardness of the first polymeric material (i.e., inner layer 33 of the distal tip 15 and the balloon 14) is generally about 63 D to about 75 D, whereas the Shore durometer hardness of the second polymeric material (i.e., outer layer 34 of the distal tip 15) is generally about 40 D to about 60 D. In a presently preferred embodiment, the first and second polymeric materials are a polyether block amide copolymer (PEBAX). More specifically, in one embodiment, the first polymeric material is a PEBAX 72D and the second polymeric material is a PEBAX 55D. The relatively high durometer material, PEBAX 72D, is a presently preferred material for the inner layer 33 of the distal tip 15. However, a lower durometer (softer) material such as PEBAX 63D can alternatively be used for the inner layer 33, but is less preferred due at least in part to the lower pull strength of the resulting distal tip, and the generally higher frictional force (or tackiness) of the softer material.

The lower durometer of the second polymeric material provides softness to the distal tip 15, and thus the outer layer 34 of the distal tip 15 typically has a relatively low flexural modulus of not greater than about 50,000 psi at room temperature. The distal tip must be flexible and soft enough to be atraumatic and allow for tracking the catheter on a guidewire in the patient's vessels during a medical procedure. The distal tip 15 is typically softer and more flexible than the portion of the shaft (e.g., the inner tubular member 23) proximally adjacent to the distal tip which defines the guidewire lumen 17 in communication with the distal tip lumen 31. In one embodiment, the proximally adjacent portion of the shaft (e.g., inner tubular member 23) has an outer layer with a higher flexural modulus than the outer layer 34 of the distal tip 15. The configuration of the distal end of the catheter 10 at the distal tip 15 preferably provides a highly flexible distal end with an improved flexibility transition, while nonetheless providing a high pull strength distal tip with a non-tacky inner surface as discussed herein.

The distal tip 15 is typically formed by coextruding the inner and outer layers 33, 34 together. Preferably, the inner layer is at most about 50% of the thickness of the tip, i.e., along the distal section of the tip 15 where the inner layer 33 and outer layer 34 remain as discrete layers after the tip 15 is fusion bonded along the proximal section 36. More specifically, the inner layer 33 thickness is typically about equal to or about 20% thinner than the outer layer 34 of the distal tip 15. As a result, there is a sufficient amount of the relatively high durometer first material present to provide a desired high tip pull strength. In one embodiment, the tip pull strength is about 0.8 to about 2.5 lbs, and more preferably is about 1 to about 2 lbs. Moreover, although the materials blend along the fused proximal section 36 of the tip, a sufficient amount of the (non-tacky) relatively high durometer first material is present in the blend to provide an inner surface which does not produce disadvantageous adhering of surfaces, such as the guidewire, thereto.

Although the first polymeric material is non-tacky at body temperature, the first polymeric material is not a lubricious polymeric material (e.g., the non-lubricious first polymeric material has a static coefficient of friction of greater than about 0.35). However, the distal tip 15 forms a relatively short section of the guidewire lumen 17, and the inner surface of the inner tubular member 23 defining the guidewire lumen 17 proximal to the tip 15 is preferably formed of a lubricious polymeric material which facilitates sliding the guidewire within the guidewire lumen 17. The distal tip 15 typically has a length of about 3 mm to about 7 mm, or about 1% to about 2.5% of the total length of the guidewire lumen 17 for a rapid exchange type catheter or about 0.2% to about 0.4% of the total length the catheter. In a presently preferred embodiment, the inner and outer layers 33, 34 of the tip 15 are approximately equal in length (i.e., equal within normal manufacturing tolerances).

Figure 5A:
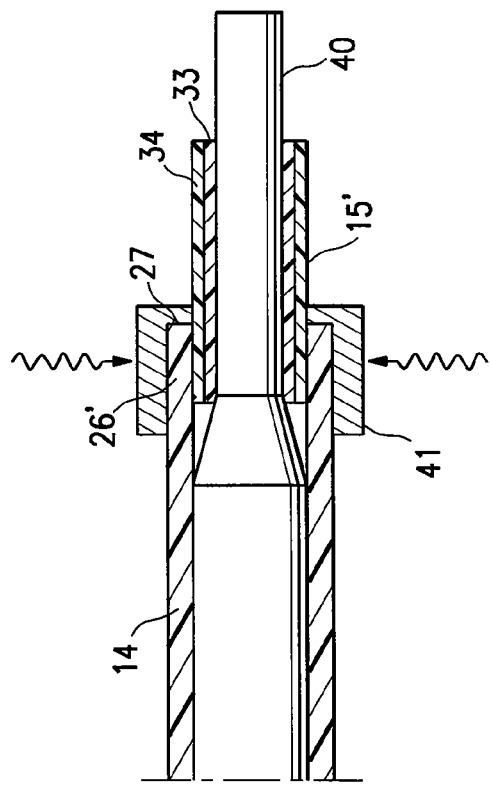
FIG. 5a illustrates a method of making a balloon catheter embodying features of the invention, during the fusion bonding of a distal tip member to a distal skirt section of the catheter balloon.

FIGS. 5a and 5b illustrate a method of making a balloon catheter with a distal tip embodying features of the invention. The corresponding reference numerals from the embodiment of FIG. 1 are used in FIGS. 5a and 5b, but with the reference numerals 15' and 26' indicating the distal tip and balloon distal skirt section, respectively, prior to being fusion bonded together in FIG. 5a. Specifically, FIG. 5a illustrates a multilayered distal tip member 15' positioned within a distal skirt section 26' of the balloon 14, to form a lap joint. The distal tip member 15' has coextruded inner and outer layers 33, 34 extending from the proximal to the distal end of the tip 15' and surrounded by the distal skirt section 26' of the balloon 14. In accordance with the invention, the inner layer 33 is formed of a first polymeric material which has a first Shore durometer hardness, and the outer layer 34 is formed of a second polymeric material which has a lower Shore durometer hardness than the first polymeric material and which is fusion bond compatible with the first polymeric material, and the balloon 14 is formed of a polymeric material fusion bond compatible with both the first and second polymeric materials. In a presently preferred embodiment, the balloon is formed at least in part of the first polymeric material.

A tapered mandrel 40 within the lumen 31 of the distal tip 15 keeps the lumen 31 open during fusion bonding of the distal tip to the balloon distal skirt section and facilitates forming the bond between the distal tip 15 and balloon skirt section 26. In a presently preferred embodiment, the process of fusion bonding the distal skirt section 26 to the distal tip member 15 is separate from the process which fusion bonds the distal skirt section 26 to the shaft inner tubular member 23. Specifically, the distal skirt section 26 is preferably fusion bonded first to the distal tip member 15, and is thereafter fusion bonded to the shaft inner tubular member 23. Alternatively, the distal skirt section 26 can be fusion bonded first to the shaft inner tubular member 23, or simultaneously fusion bonded to the distal tip and shaft inner tubular member.

The method includes applying heat and a radially inward force (indicated by arrows in the figures) on an outer surface of a distal portion of the balloon distal skirt section 26', which fusion bonds an inner surface of the distal skirt section to the outer surface of the distal tip member 15' in the embodiment of FIG. 5a. A heat shrink sheath 41 is on the distal portion of the distal skirt section 26' during fusion bonding to the tip 15'. The heat shrink sheath 41 shrinks when heated, to apply the inward force pressing the distal skirt section 26' against the distal tip 15'. The heat shrink sheath 41 is removed and discarded after the fusion bonding is completed. As discussed above, the resulting fusion bonded proximal section 36 of the tip 15 is a fused blend of the balloon distal skirt section and the inner and outer layers of the tip, and the fused blend has both the outer layer and inner layer of the distal tip fused with the material of the distal skirt section 26 along the proximal section 36 of the tip.

The heat applied during fusion bonding of the distal tip is not less than the glass transition temperature of the first polymeric material, and the heat and force are sufficient to cause the polymeric materials of the inner and outer layers of the tip to melt or flow along the proximal section thereof. Although the outer surface of the inner layer 33 was separated from the inner surface of the balloon distal skirt section by the outer layer 34 prior to the fusion bonding, the materials are compatible and soften or melt and flow sufficiently such that the inner layer material contacts and fusion bonds to the distal skirt section material in the resulting blend along fused section 36.

The method includes bonding (e.g., adhesively and/or fusion bonding) the balloon distal skirt section to the elongated shaft 11 (e.g., inner tubular member 23). Preferably, the bonding comprises applying heat and a radially inward force on an outer surface of a proximal portion of the balloon distal skirt section 26 (see FIG. 5b), to thermally bond the distal skirt section to the elongated shaft inner tubular member 23. In a presently preferred embodiment, the distal skirt section is fusion bonded to the elongated shaft 11 without an adhesive there between, although in an alternative embodiment an adhesive may be provided between the mating surfaces of the inner tubular member and distal skirt section to strengthen the bond. In FIG. 5b, a heat shrink sheath 42 similar to sheath 41 of FIG. 5a applies a radially inward force on the proximal portion of the distal skirt section 26 during bonding to the shaft inner tubular member 23, and is thereafter removed along with mandrel 44, leaving the distal skirt section 26 bonded to the inner tubular member 23. As discussed above, in one embodiment, the bonding of the shaft inner tubular member 23 to the balloon distal skirt section 26 occurs after the distal skirt section 26 has been fusion bonded to the distal tip 15, and as a result, the proximal portion of the balloon distal skirt section is located proximal to the (already) fusion bonded distal tip member 15. The heat and radially inward force is applied to the proximal and distal portions of the distal skirt section 26 but is preferably not focused onto the portion there between which extends over the gap between the inner tubular member 23 and distal tip member 15. In the embodiment illustrated in FIG. 1, the resulting balloon catheter has the distal end of the inner tubular member 23 and the proximal end of the distal tip 15 spaced apart by a gap there between which is not completely filled up by polymeric material caused to soften and flow during the bonding process.

The dimensions of catheter 10 are determined largely by the size of the balloon and guidewire to be employed, the catheter type, and the size of the artery or other body lumen through which the catheter must pass or the size of the stent being delivered. Typically, the outer tubular member 22 has an outer diameter of about 0.025 to about 0.04 inch (0.064 to 0.10 cm), usually about 0.037 inch (0.094 cm), and the wall thickness of the outer tubular member 22 can vary from about 0.002 to about 0.008 inch (0.0051 to 0.02 cm), typically about 0.003 to 0.005 inch (0.0076 to 0.013 cm). The inner tubular member 23 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 14 has a length about 0.8 cm to about 6 cm, and an inflated working diameter of about 2 to about 10 mm.

Inner tubular member 23 and outer tubular member 22 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. The inner tubular member 23 and outer tubular member 22 are typically multilayered tubing, or sections of tubing joined end-to-end, as is conventionally known for balloon catheter shafts. Although the shaft is illustrated as having an inner and outer tubular member, a variety of suitable shaft configurations may be used including a dual lumen extruded shaft having a side-by-side lumens extruded therein. Additionally, the outer tubular member 23 typically includes supporting members including a high strength member such as a hypotube in the proximal shaft section and/or across the guidewire proximal port 18 (not shown). Similarly, although the embodiment illustrated in FIG. 1 is a rapid exchange catheter, in one embodiment (not shown) the catheter of this invention is an over-the-wire type balloon catheter having the guidewire lumen extending from the guidewire distal port at the catheter distal end to a guidewire proximal port at the proximal end of the catheter.

While the present invention is described herein in terms of certain preferred embodiments, those skilled in the art will recognize that various modifications and improvements may be made to the invention without departing from the scope thereof. For example, although discussed in terms of an embodiment in which the distal tip member 15 is fusion bonded to the balloon distal skirt section 26, in one embodiment an outer sheath member in place of the balloon distal skirt section forms the fusion bond to at least the proximal portion of the distal tip member, with the outer sheath member extending distally from the distal end of a balloon distal skirt section and preferably being formed of the first polymeric material. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

We claim:

1. A method of making a balloon catheter having an elongated shaft with an inflation lumen and a guidewire lumen, and a balloon sealingly secured to a distal shaft section, comprising:
   a) placing a distal tip member and a balloon having a distal skirt section and an inner lumen on a mandrel;
   b) positioning a proximal end of the distal tip member within the distal skirt section of the balloon, the distal tip member having coextruded inner and outer layers extending from the proximal end of the tip, and the inner layer is formed of a first polymeric material which has a first Shore durometer hardness, and the outer layer is formed of a second polymeric material which has a lower Shore durometer hardness than the first polymeric material and which is fusion bond compatible with the first polymeric material, and the balloon is formed at least in part of a polymeric material fusion bond compatible with the first and second polymeric materials of the tip;
   c) applying heat and a radially inward force on an outer surface of a distal portion of the balloon distal skirt section to fusion bond the distal skirt section to the proximal end of the distal tip member, such that a proximal section of the bonded tip is a fused blend of the balloon distal skirt section and the inner and outer layers of the tip, the fused blend having both the outer layer and inner layer of the tip fused with the material of the distal skirt section along the proximal section of the tip to form a lap joint securing the tip to the balloon distal skirt section;
   d) placing an elongate shaft on a mandrel such that the elongate shaft is co-axially disposed within the inner lumen of the balloon after the distal tip member has been fusion bonded to the distal skirt section of the balloon;
   e) positioning the distal end of the elongate shaft such that the proximal end of the distal tip member is longitudinally spaced apart from the elongated shaft by a gap there between; and
   f) applying heat and a radially inward force on an outer surface of a proximal portion of the balloon distal skirt section, located proximal to the fusion bonded distal tip member, to bond the distal skirt section to the elongated shaft.

2. The method of claim 1 wherein the heat applied in c) is not less than the glass transition temperature of the first polymeric material, and the heat and force are sufficient to melt the inner and outer layers of the tip along the proximal section thereof.

3. The method of claim 1 wherein the distal tip member is positioned in b) such that a distal end of the balloon distal skirt section is proximal to a distal end of the first layer and a distal end of the second layer of the tip.

4. The method of claim 1 wherein an adhesive extends along the proximal portion and does not extend along the distal portion of the balloon distal skirt section, such that f) includes forming an adhesive bond between the proximal portion of the balloon distal skirt section and the shaft.

5. The method of claim 1 wherein both the inner layer and outer layer of the distal tip member extend along a distal section of the distal tip member to the distal end thereof.

6. The method of claim 1 wherein the inner and outer layers of the distal tip are approximately equal in length.

7. The method of claim 1 wherein the distal tip has a pull strength of about 0.5 to about 2.5 lbs.

8. The method of claim 1 wherein the balloon is formed at least in part of the first polymeric material.

9. The method of claim 1 wherein the balloon is a single-layer balloon formed of the first polymeric material.

10. The method of claim 1 wherein the first and second polymeric materials are a polyether block amide copolymer.

11. The method of claim 1 wherein the first polymeric material is not a lubricious polymeric material, and an inner surface of the shaft defining the guidewire lumen proximal to the tip is formed of a lubricious polymeric material.

12. The method of claim 1 wherein the second polymeric material of the distal tip provides a surface which has a higher tackiness than the first polymeric material of the distal tip, such that the inner surface of the distal tip at least along the distal section thereof is not tacky at a body temperature above room temperature.

13. A method of making a balloon catheter having an elongated shaft with an inflation lumen and a guidewire lumen, and a balloon sealingly secured to a distal shaft section, comprising:
   a) placing a distal tip member and a balloon having a distal skirt section and an inner lumen on a mandrel;

b) positioning a proximal end of the distal tip member within the distal skirt section of the balloon, the distal tip member having coextruded inner and outer layers extending from a proximal end to a distal end of the distal tip member, the inner layer formed of a first polymeric material which has a first Shore durometer hardness, and the outer layer formed of a second polymeric material which has a lower Shore durometer hardness than the first polymeric material and which is fusion bond compatible with the first polymeric material, and the balloon is formed at least in part of a polymeric material fusion bond compatible with the first and second polymeric materials of the tip;

c) applying heat and a radially inward force on an outer surface of a distal portion of the balloon distal skirt section to fusion bond the distal skirt section to the proximal end of the distal tip member, such that a proximal section of the bonded tip is a fused blend of the balloon distal skirt section and the inner and outer layers of the tip, the fused blend having both the outer layer and inner layer of the tip fused with the material of the distal skirt section along the proximal section of the tip to form a lap joint securing the tip to the balloon distal skirt section;

d) placing an elongate shaft on a mandrel such that the elongate shaft is co-axially disposed within the inner lumen of the balloon after the distal tip member has been fusion bonded to the distal skirt section of the balloon;

e) positioning the distal end of the elongate shaft such that the proximal end of the distal tip member is longitudinally spaced apart from the elongated shaft by a gap there between; and f) applying heat and a radially inward force on an outer surface of a proximal portion of the balloon distal skirt section, located proximal to the fusion bonded distal tip member, to bond the distal skirt section to the elongated shaft.

14. A method of making a balloon catheter having an elongated shaft with an inflation lumen and a guidewire lumen, and a balloon sealingly secured to a distal shaft section, comprising:

a) placing a distal tip member and a balloon having a distal skirt section and an inner lumen on a mandrel;

b) positioning a proximal end of the distal tip member in contact with the distal skirt section of the balloon, the distal tip member having coextruded inner and outer layers extending from the proximal end of the tip, and the inner layer is formed of a first polymeric material which has a first Shore durometer hardness, and the outer layer is formed of a second polymeric material which has a lower Shore durometer hardness than the first polymeric material and which is fusion bond compatible with the first polymeric material, and the balloon is formed at least in part of a polymeric material fusion bond compatible with the first and second polymeric materials of the tip;

c) placing a first heat shrink sleeve over the distal portion of the balloon skirt section;

d) applying heat the heat shrink sleeve to fusion bond the distal skirt section to the proximal end of the distal tip member, such that a proximal section of the bonded tip is a fused blend of the balloon distal skirt section and the inner and outer layers of the tip, the fused blend having both the outer layer and inner layer of the tip fused with the material of the distal skirt section along the proximal section of the tip;

e) placing an elongate shaft on a mandrel such that the elongate shaft is co-axially disposed within the inner lumen of the balloon after the distal tip member has been fusion bonded to the distal skirt section of the balloon;

f) positioning the distal end of the elongate shaft such that the proximal end of the distal tip member is longitudinally spaced apart from the elongated shaft by a gap there between;

g) placing a second heat shrink sleeve over a proximal portion of the balloon skirt section; and h) applying heat the heat shrink sleeve to bond the distal skirt section to the elongated shaft.

15. The method of claim 14 wherein the first heat shrink sleeve provides at least some inward force on the outer surface of the distal portion of the balloon skirt section.

16. The method of claim 14 wherein the first heat shrink sleeve is removed from the distal portion of the balloon skirt section after heat is applied in accordance with d).

17. The method of claim 14 wherein the second heat shrink sleeve provides at least some inward force on the outer surface of the proximal portion of the balloon skirt section.

18. The method of claim 14 wherein the second heat shrink sleeve is removed from the proximal portion of the balloon skirt section after heat is applied in accordance with h).

* * * * *

UNITED STATES PATENT AND TRADEMARK OFFICE
CERTIFICATE OF CORRECTION

PATENT NO. : 8,444,802 B2  
APPLICATION NO. : 12/468745  
DATED : May 21, 2013  
INVENTOR(S) : Jeong S. Lee et al.

Page 1 of 1

It is certified that error appears in the above-identified patent and that said Letters Patent is hereby corrected as shown below:

In the Claim

Claim 14, Column 12, line 13, between "heat" and "the" insert --on--.
line 31, between "heat" and "the" insert --on--.

Signed and Sealed this
Seventh Day of January, 2014

Margaret A. Focarino
*Commissioner for Patents of the United States Patent and Trademark Office*